United States Patent [19]
Galperin

[11] Patent Number: 5,905,181
[45] Date of Patent: May 18, 1999

[54] PROCESS FOR THE ISOMERIZATION OF PARAFFINS

[75] Inventor: Leonid B. Galperin, Wilmette, Ill.

[73] Assignee: UOP LLC, Des Plaines, Ill.

[21] Appl. No.: 08/998,930

[22] Filed: Dec. 29, 1997

[51] Int. Cl.$^6$ ........................................... C07C 5/13
[52] U.S. Cl. ........................ 585/734; 585/739; 585/751
[58] Field of Search ................... 585/734, 739, 585/751

[56] References Cited

U.S. PATENT DOCUMENTS

| | | | |
|---|---|---|---|
| 4,158,676 | 6/1979 | Smith et al. | 585/481 |
| 4,419,220 | 12/1983 | LaPierre et al. | 208/111 |
| 5,100,535 | 3/1992 | Chen et al. | 208/111 |
| 5,275,720 | 1/1994 | Ward | 208/111 |
| 5,419,830 | 5/1995 | Chou et al. | 208/111 |

*Primary Examiner*—Glenn Caldarola
*Assistant Examiner*—In Suk Bullock
*Attorney, Agent, or Firm*—Thomas K. McBride; Frank S. Molinaro

[57] ABSTRACT

A paraffin isomerization process is described and claimed. The process involves contacting the paraffins with an isomerization catalyst at isomerization conditions. Additionally, the process requires the injection of a nitrogen containing compound such as an amine, e.g., t-butylamine, and raising the operating temperature by about 20° C. to about 150° C. The effect of these modifications is to provide improved selectivity and sulfur resistance to the catalyst.

8 Claims, No Drawings

PROCESS FOR THE ISOMERIZATION OF PARAFFINS

FIELD OF THE INVENTION

This invention relates to a process for the isomerization of paraffins. The process involves contacting the paraffins with a catalyst at isomerization conditions. Crucial parameters of the process are the injection of a nitrogen containing compound and raising the operating temperature by about 20° C. to about 150° C.

BACKGROUND OF THE INVENTION

Paraffinic oils containing $C_{10+}$ (ten carbons or higher) compounds find various uses as lubricating oils, heating oils, jet fuels, etc. One requirement of these oils is that they have a low viscosity or pour point at low temperatures. However, these paraffin mixtures usually contain straight chain or slightly branched paraffins which are waxes at lower temperatures which result in the paraffin mixture having a high pour point or viscosity at the lower temperatures. In order to remove these waxes, various processes are used to dewax the paraffin feed. Dewaxing processes include catalytic cracking where the long chain paraffins are cracked to smaller chain paraffins and isomerization where the straight chained paraffins are isomerized to branched paraffins.

Dewaxing by isomerization is disclosed in U.S. Pat. No. 4,419,220. The isomerization catalyst which is used is a zeolite beta having a silica: alumina ratio of at least 30:1 and having a hydrogenation component such as platinum. It is further disclosed that lower temperatures favor isomerization over cracking and therefore, lower temperatures are preferred. The '220 patent also discloses a preliminary hydrotreating step to remove nitrogen and sulfur compounds in order to improve catalyst performance and permit operation at lower temperatures.

As the '220 patent discloses, a bifunctional catalyst is used in order to achieve high isomerization selectivity. The two functions are hydrogenation and isomerization. Hydrogenation (and dehydrogenation) is carried out by the metal function, e.g., platinum, palladium, nickel, etc., while isomerization is carried out by the acid function, e.g., zeolites, Si—Al, etc.

The specific steps in paraffin isomerization are as follows. First, the paraffin is dehydrogenated on the metal function to give an olefin. The olefin reacts with the acid function to give a n-carbenium ion which is isomerized to an iso-carbenium ion. Next the iso-carbenium ion will be converted to an iso-olefin followed by hydrogenation to an iso-paraffin. Additionally, the iso-paraffins can be cracked on the acid sites to give low molecular weight paraffins and low molecular weight carbenium ions which will in turn be hydrogenated to light paraffins. Competition between hydrogenation and cracking explains product distribution. To maintain the high isomerization activity the hydrogenation function of the catalyst should be high enough to convert the intermediate carbenium ions to iso-paraffins and prevent their cracking. In the presence of sulfur hydrogenation activity will be suppressed owing to formation of metal sulfides with low hydrogenation activity and thus cracking will dominate resulting in low isomerization selectivity and the formation of light paraffins. Accordingly, there is a need for an isomerization catalyst/process which can function well in the presence of sulfur.

Applicant has found a solution to this problem which involves injection of a nitrogen containing compound, e.g., ammonia, into the isomerization reactor and simultaneously increasing the temperature by about 20° C. to about 150° C.

There are several references which disclose the use of nitrogen compounds in refining processes. For example, U.S. Pat. No. 5,419,830 discloses the use of ammonia to control the temperature in the reactor and prevent temperature runaway. U.S. Pat. No. 4,158,676 discloses the isomerization of monocyclic methyl-substituted aromatic hydrocarbon compounds in which nitrogen containing compounds are injected. U.S. Pat. No. 5,275,720 describes a two stage hydrocracking process in which ammonia is injected in the first stage to increase catalyst cracking activity.

In contrast to these references, applicant's process combines the injection of a nitrogen containing compound with an increase in the operating temperature. Increasing the temperature is contrary to the teachings in the art which state that lower temperatures favor isomerization. This results in improved selectivity and sulfur tolerance.

SUMMARY OF THE INVENTION

As stated the present invention relates to an improved isomerization process. Accordingly one embodiment of the invention is a process for the isomerization of paraffins in the presence of sulfur compounds, comprising contacting the paraffins with a catalyst at a temperature of about 20° C. to about 150° C. higher than the normal temperature of about 250° C. to about 500° C., a pressure of about atmospheric to about 25,000 kPa, a hydrogen to paraffin volume ratio of about 200 to about 4,000 std $m^3/m^3$, a space velocity of about 0.1 to about 10 $hr^{-1}$ and injecting from about 5 to about 50,000 ppm nitrogen present as a nitrogen containing compound thereby improving the selectivity and sulfur resistance of the catalyst.

This and other objects and embodiments will become clear after a more detailed description of the invention.

DETAILED DESCRIPTION OF THE INVENTION

One essential feature of the present invention is an isomerization catalyst. The catalyst comprises a refractory inorganic oxide, the oxide having dispersed thereon a hydrogenation component and, optionally, a binder. The refractory inorganic oxide is selected from, but not limited to, SAPO and MeAPSO molecular sieves, zeolites, especially MFI, and amorphous Si—Al.

SAPO is an acronym for a silicoaluminophosphate molecular sieve. The preparation and characterization of SAPO's is described in U.S. Pat. No. 4,440,871, which is incorporated by reference. The SAPO molecular sieves are identified by a numbering system which refers to a specific structure, e.g., SAPO-5, SAPO-11, etc., which is also described in the '871 patent. MeAPSO is an acronym for metal aluminumsilicophosphate molecular sieves where Me is selected from the group consisting of magnesium, manganese, cobalt, iron, zinc, and mixtures thereof. MeAPSOs are described in U.S. Pat. No. 4,793,984 which is incorporated by reference. The specific molecular sieves are also described in the following patents: MgAPSO or MAPSO—U.S. Pat. No. 4,758,419. MnAPSO—U.S. Pat. No. 4,686,092; CoAPSO—U.S. Pat. No. 4,744,970; FeAPSO—U.S. Pat. No. 4,683,217 and ZnAPSO—U.S. Pat. No. 4,935,216, all of which are incorporated by reference. A preferred MeAPSO support is MAPSO (M=Mg) and a preferred MAPSO is MAPSO-31 where 31 means a MAPSO molecular sieve having structure type 31. This numbering system is also described in the above incorporated patents.

Among the zeolites which can be used are MFI and ferrierite. MFI is the International Zeolite Association designation for ZSM-5 or silicalite. ZSM-5 is described in U.S. Pat. No. 3,702,886 which is incorporated by reference.

Silicalite is described in U.S. Pat. Nos. 4,061,724 and 4,073,865 which are incorporated by reference. ZSM-5 is represented by the empirical formula:

$$(0.9\pm0.2)M_2O/n: Al_2O_3:xSiO_2$$

where M is an alkali metal cation and x is at least 5. For use in the present invention, x is greater than 50. That is the $SiO_2/Al_2O_3$ ratio is greater than 50 or the Si/Al ratio is greater than 100.

Another oxide which can be used is an amorphous silica-alumina (Si—Al). This amorphous material is not a physical mixture of silica and alumina but is an acidic and amorphous material that has been cogelled or coprecipitated. This term and details regarding the preparation can be found in U.S. Pat. Nos. 3,909,450; 3,274,124 and 4,988,659 which are incorporated by reference.

Any of the oxides enumerated above can be formed into any desired shapes such as pills, cakes, extrudates, powders, granules, spheres, etc. and they may be utilized in any particular size. The oxide is formed into the particular shape by means well known in the art. In making the various shapes, it may be necessary to mix the oxide with a binder. Examples of binders which can be used include but are not limited to alumina, silica, silica-alumina (see above) and mixtures thereof. Usually the oxide and binder are mixed along with a peptizing agent such as HCl, $HNO_3$, KOH, etc. to form a dough. This dough is extruded through a suitably shaped and sized die to form extrudate particles, which are dried and calcined. Calcination is normally carried out at a temperature of about 260° C. to about 650° C. for a period of about 0.5 to about 2 hours. The amount of binder which is present in the composite can vary from about 10 to about 90 wt. % of the composite and preferably from about 30 to about 70 wt. %. Additionally, the oxide support can be formed into spheres using the well known oil drop method. This method is preferred for the preparation of amorphous silica-alumina spheres and is described in U.S. Pat. No. 4,497,704 which is incorporated by reference. Note that in this case no binder is used.

Another essential element of the catalyst of this invention is a hydrogenation component which is a Group VIII metal. The Group VIII metals which can be used include platinum, palladium, rhodium, iridium, osmium, ruthenium, iron, cobalt, nickel and mixtures thereof. Preferred Group VIII metals are platinum and palladium. The Group VIII metal is dispersed onto the support by means well known in the art such as spray impregnation or evaporative impregnation. Both spray or evaporative impregnation use a solution containing a decomposable compound of the desired noble metal. By decomposable is meant that upon heating the compound decomposes to provide the noble metal or noble metal oxide. Examples of decomposable compounds which can be used include chloroplatinic acid, palladic acid, chloroiridic acid, rhodium trichloride, rutherium tetrachloride, osmium trichloride, rhodium nitrate, ammonium chloroplatinate, platinum tetrachloride hydrate, palladium chloride, palladium nitrate, tetraamine platinum chloride, tetraamminepalladium (II) chloride, iron chloride, cobalt chloride, nickel chloride, iron nitrate, cobalt nitrate and nickel nitrate. The solvent which is used to prepare the solution is usually water although organic solvents such as alcohols, dimethyl formamide (DMF), dimethylsulfoxide (DMSO), tetrahydrofuran (THF) and amines, e.g., pyridine, can be used. Spray impregnation involves taking a small volume of the solution and spraying it over the support while the support is moving. When the spraying is over, the wetted support can be transferred to other apparatus for drying or finishing steps.

One particular method of evaporative impregnation involves the use of a steam-jacketed rotary dryer. In this method the support is immersed in the impregnating solution which has been placed in the dryer and the support is tumbled by the rotating motion of the dryer. Evaporation of the solution in contact with the tumbling support is expedited by applying steam to the dryer jacket. The impregnated support is then dried at a temperature of about 60° C. to about 300° C. and then calcined at a temperature of about 300° C. to about 850° C. for a time of about 30 minutes to about 8 hours to give the calcined catalyst.

The amount of Group VIII metal deposited onto the oxide can vary considerably from about 0.05 to about 10 wt. % of the catalyst. Specifically, when the noble metal is platinum, the amount dispersed on the catalyst varies from about 0.2 to about 1.0 wt. %.

The catalyst described above is now used to isomerize long chained paraffins. A variety of feedstocks can be treated using the catalyst described above including reduced crudes, vacuum tower residue, cycle oils, FCC tower bottoms, gas oils, vacuum gas oils and other heavy oils. The feed will normally be a $C_{10}$+ feedstock since lighter oils will usually be free of significant quantities of waxy components. However, the process is particularly useful with waxy distillate stocks such as gas oils, kerosenes, jet fuels, lubricating oil stocks, heating oils and other distillate fractions whose pour point and viscosity need to be maintained within certain specification limits. Lubricating oil stocks will generally boil at about 230° C. (450° F.), more usually above 315° C. (600° F.). Hydrocracked stocks are a convenient source of stocks of this kind and also of other distillate fractions since they normally contain significant amounts of waxy n-paraffins which have been produced by the removal of polycyclic aromatics. The feedstock for the present process will normally be a $C_{10}$+ feedstock and more specifically one containing $C_{10}$ to $C_{40}$ hydrocarbons. These feedstocks will contain paraffins, olefins, naphthenes, aromatics and heterocyclic compounds, with a substantial proportion of higher molecular weight n-paraffins and slightly branched paraffins which contribute to the waxy nature of the feedstock. The feedstock will also contain some amount of sulfur, ranging from a few parts per million (ppm) to several thousand ppm.

The feedstock is contacted with the catalyst in a reactor in which the catalyst is present as stationary bed, a fluidized bed or any other type of catalyst bed. Usually the contacting is carried out at a temperature of about 250° C. to about 500° C., but in the instant invention, the temperature is raised from about 20° C. to about 150° C. above these "normal" or "usual" temperatures, which is typical for hydrotreated feedstocks containing no, or substantially no, sulfur. That is, the operating temperature is determined by the type of feedstock which is used, the relative activity of the catalyst, the amount of sulfur in the feed, pressure, $H_2$/HC ratio, etc. Once this temperature is determined, the temperature is raised from about 20° C. to about 150° C. depending on the amount of nitrogen compound added and the relative activity of the catalyst. The greater the amount of nitrogen compound, the higher the temperature must be raised.

Pressures range from atmospheric to about 25,000 kPa (3,600 psig) and preferably from about 4,000 to about 10,000 kPa (565 to 1,435 psig). Liquid Hourly Space Velocity (LHSV) ranges from about 0.1 to about 10 $hr^{-1}$ and preferably from about 0.2 to about 5 $hr^{-1}$. Hydrogen is also added in a hydrogen: feedstock volume ratio of about 200 to about 4,000 std.m$^3$/m$^3$ (1,125 to 22,470 SCF/bbl) preferably 600 to 2,000 std.m$^3$/m$^3$ (3,370 to 11,235 SCF/bbl).

The instant process also requires the injection of a basic nitrogen containing compound into the reactor. The compounds that can be used include ammonia and organic nitrogen containing compounds such as alkyl amines, aromatic amines, heterocyclic nitrogen-containing compounds, amides, etc. Specifically the alkyl amines can contain 1 to 30 carbon atoms and preferably 1 to 8 carbon atoms. Examples include methyl amine, tertiary butyl amine, ethyl amine, ethyl butylamine, tripropylamine, triethanolamine, cyclohexylamine, di-n-propylamine, neopentylamine, di-n-pentylamine, etc. Aromatic amines with 6 to 50 carbon atoms are within the invention and include aniline, diphenylamine, N-methyl-N-ethylamine, p-toluidine, p-phenylene-diamine, N-methylaniline, dimethylaniline, etc. Heterocyclic nitrogen compounds include pyridine, pyrolidine, quinoline, piperidine, piperazine, pyrrole, pyrellidine, etc. Amides include dimethyl formade, N-phenyl-acetamide, N-methyl-N-ethylbenzamide, etc.

The nitrogen containing compound can be cofed with the paraffin feedstock or can be directly injected into the reactor. Injection into the reactor can be done using one injection port or multi-injection ports. Regardless of which method is used to introduce the nitrogen containing compound, the amount of nitrogen containing compound which is introduced is that amount which give from about 5 to about 50,000 ppm and preferably from about 10 ppm to about 1,000 ppm nitrogen.

In order to more fully illustrate the invention, the following examples are set forth. It is to be understood that the examples are not intended as an undue limitation on the broad scope of the invention as set forth in the appended claims.

EXAMPLE 1

MAPSO-31 was prepared according to U.S. Pat. No. 4,758,419. Platinum was dispersed onto the MAPSO-31 support as follows. An aqueous solution containing sufficient tetraamineplatinum chloride to give 0.4 wt. % Pt on the final catalyst was used to ion exchange platinum onto MAPSO-31 by contacting the solution with the MAPSO-31 powder for a time of about 4 hours at a temperature of about 70° C. The ion exchanged powder was mixed with peptized alumina in a ratio of 80:20 (MAPSO-31:Al$_2$O$_3$), the resultant dough was extruded and dried at 120° C. for 8 hours. Finally, the dried material was calcined in air at 500° C. for 4 hours. The catalyst was identified as catalyst A.

EXAMPLE 2

SAPO-11 was prepared according to the procedure in U.S. Pat. No. 4,440,871. The SAPO-11 was mixed with alumina (60:40 wt. ratio), water and nitric acid, mixed and then extruded. The wet extrudates were dried at 100° C. for 24 hours and calcined in air at 600° C. for 3 hours to give the SAPO-11/Al$_2$O$_3$ support.

The SAPO-11/Al$_2$O$_3$ support was impregnated with an aqueous solution containing sufficient chloroplatinic acid to give 0.4 wt. % Pt (with respect to alumina) as follows. In a rotary evaporator the support and solution were mixed in a 1:1 volume ratio, rotated at room temperature for one hour and then heated with steam to evaporate the excess water. The impregnated support was dried at 120° C. and then calcined at 500° C. for 4 hours. This catalyst was identified as catalyst B.

EXAMPLE 3

A spherical support of cogelled silica-alumina with 35% SiO$_2$ and 65% Al$_2$O$_3$ was prepared as in U.S. Pat. No. 4,497,704. The spherical support was impregnated with 0.4 wt. % platinum as in Example 2. This catalyst was identified as catalyst C.

EXAMPLE 4

The catalysts described above were tested for C-10 hydroisomerization as follows. A sample containing 5 grams of catalyst and 5 g of quartz were mixed and placed in a reactor. Next, the catalyst was reduced in situ in one of three ways. If the test involved a clean feed, i.e., no sulfur or nitrogen, then the catalyst was reduced using a H$_2$ stream at 400° C. for 4 hours. If the test involved adding sulfur to the feedstream, then the catalyst was pretreated using a H$_2$/H$_2$S (85/f15) stream at 400° C. for 4 hours. Finally, if the test involved using both sulfur and nitrogen, then the catalyst was first reduced using a H$_2$ stream containing 1,000 ppm NH$_3$ and then this stream was replaced with a H$_2$ stream containing 1,000 ppm of H$_2$S at 400° C. for 4 hours.

A feed containing n-C$_{10}$ plus hydrogen at a ratio of H$_2$/hydrocarbon of 1000 SCFB was downflowed through the catalyst at a LHSV of 25 g/hr and a pressure of 3448 kpag (500 psig). The reactor was ramped up to a certain temperature and lined out at that temperature for 5 hours. At that point the effluent was analyzed by gas chromatography to determine the percent of n-C$_{10}$. converted, i.e., disappearance of n-C$_{10}$ and the selectivity to I-C$_{10}$. Any component having a carbon number less than 10 is a cracked component and undesirable.

When sulfur was added, it was added at 1000 ppm as H$_2$S and mixed with the hydrogen. In the case where nitrogen was added, it was added as tertiary butyl amine (TBA) present in the n-C$_{10}$ feed. The amount of TBA added was such as to give 770 ppm N in the feed. The results of this test are presented in the Table. What is presented is the temperature needed to reach 50% conversion and selectivity to iso-C$_{10}$ at that temperature.

TABLE

Effect of Nitrogen and Sulfur on Catalyst Selectivity

| Catalyst I.D. | Temp (° C.) at 50% Conv. | Selectivity (%) to iso-C$_{10}$ | H$_2$S (ppm) | N (ppm) |
|---|---|---|---|---|
| A | 330 | 82 | 0 | 0 |
| A | 378 | 53 | 1000 | 0 |
| A | 422 | 75 | 0 | 770 |
| A | 433 | 84 | 1000 | 770 |
| B | 328 | 97 | 0 | 0 |
| B | 397 | 97 | 1000 | 770 |
| C | 384 | 95 | 0 | 0 |
| C | 442 | 95 | 1000 | 770 |

The results in the Table show that the presence of sulfur alone increases the temperature needed to 50% conversion and severely decreases the selectivity to iso-C$_{10}$. The presence of nitrogen alone also decreases selectivity but not as much as sulfur alone. However, by introducing nitrogen when sulfur is present, one obtains the same selectivity versus the case where neither is present, but at a higher temperature.

I claim as my invention:

1. A process for the isomerization of paraffins in the presence of sulfur compounds comprising contacting the paraffins with a catalyst at a temperature of about 20° C. to about 150° C. higher than the normal temperature of about 250° to about 500° C., a pressure of about atmospheric to about 25,000 kPa, a hydrogen to paraffin volume ratio of about 200 to about 4,000 std $m^3/m^3$, a space velocity of about 0.1 to about 10 $hr^{-1}$ and injecting from about 5 to about 50,000 ppm of nitrogen present as a nitrogen containing compound thereby improving the selectivity and sulfur resistance of the catalyst, the catalyst consisting essentially of a Group VIII metal dispersed on an inorganic oxide support selected from the group consisting of MeAPSO, SAPO, amorphous Si—Al and ferrierite and MFI zeolites having a Si/Al ratio of at least 100.

2. The process of claim 1 where the catalyst also contains a binder.

3. The process of claim 1 where the Group VIII metal is selected from the group consisting of platinum, palladium, rhodium, iridium, osmium, ruthenium, iron, cobalt, nickel and mixtures thereof.

4. The process of claim 3 where the Group VIII metal is selected from the group consisting of platinum, palladium or mixtures thereof.

5. The process of claim 1 where the Group VIII metal is present in an amount from about 0.05 to about 10 wt. % of the catalyst.

6. The process of claim 3 where the Group VIII metal is platinum and is present in an amount from about 0.2 to about 1.0 wt. % of the catalyst.

7. The process of claim 1 where the paraffins are $C_{10}$ to $C_{40}$ paraffins.

8. The process of claim 1 where the amount of nitrogen varies from about 10 to about 1,000 ppm.

* * * * *